(12) United States Patent
Richardson et al.

(10) Patent No.: US 8,384,886 B2
(45) Date of Patent: Feb. 26, 2013

(54) FIBER OPTIC BUILDING MONITORING SYSTEM

(75) Inventors: Paul Richardson, Austell, GA (US); David G. Koch, Mableton, GA (US)

(73) Assignee: Prosensor Technology, LLC, Mableton, GA (US)

( * ) Notice: Subject to any disclaimer, the term of this patent is extended or adjusted under 35 U.S.C. 154(b) by 275 days.

(21) Appl. No.: 12/897,480

(22) Filed: Oct. 4, 2010

(65) Prior Publication Data
US 2011/0194102 A1     Aug. 11, 2011

Related U.S. Application Data

(60) Provisional application No. 61/337,713, filed on Feb. 9, 2010.

(51) Int. Cl.
*G01N 21/00* (2006.01)
(52) U.S. Cl. ......................................... 356/73.1
(58) Field of Classification Search ................ None
See application file for complete search history.

(56) References Cited

U.S. PATENT DOCUMENTS 5,567,932 A * 10/1996 Staller et al. ............. 250/227.14
2010/0289651 A1 * 11/2010 Beinhocker .................. 340/600

* cited by examiner

*Primary Examiner* — Tu Nguyen
(74) *Attorney, Agent, or Firm* — Michael J. Mehrman; Mehrman Law Office, P.C.

(57) ABSTRACT

A building roof monitoring system that includes a fiber optic filament positioned between a water barrier layer (e.g., roof membrane) and a roof substrate layer of the building roof. The fiber optic filament may be part of a sensing layer that includes the fiber optic filament carried by a water transport layer configured to draw water coming into contact with the water transport layer into contact with the fiber optic filament. An optical analyzer injects laser light into the fiber optic filament and detects changes in propagation of the laser light through the fiber optic filament indicative of water coming in contact with the fiber optic filament to detect a roof leak. A response system including a controller, alarm or remote communication unit operatively connected to the optical analyzer responds to the roof leak detected by the optical analyzer.

20 Claims, 7 Drawing Sheets

FIBER OPTIC BUILDING MONITORING SYSTEM

REFERENCE TO RELATED APPLICATIONS

The present invention claims priority to U.S. Provisional Patent Application Ser. Nos. 62/337,718 and 61/337,713, both filed Feb. 9, 2010, which are incorporated herein by reference.

FIELD OF THE INVENTION

The present invention relates generally to building monitoring systems and, more particularly, relates to a fiber optic moisture, temperature, and strain measuring system suitable for use as a roof leak detection system.

BACKGROUND OF THE INVENTION

The present invention is a fiber optic product designed for monitoring the health of a building and, more particularly, for the early detection of unwanted changes in moisture and temperature that are commonly associated with roof leaks. According to construction industry publications, approximately 70% of construction litigation costs involve the roof system. Further, it is commonly asserted that up to 75% of all new roof systems leak within the first five years. Early and reliable roof leak detection is therefore a problem of paramount importance for building monitoring and maintenance.

The problem of detection of leaks in roofs is primarily addressed today via three methods:
 1. Thermograph imaging: Specialized equipment using thermographic imaging (heat imaging via thermal imaging cameras) to discover relative leak location after water penetration has been reported.
 2. Vector Field Mapping (VFM): Electric charge through a wire buried below the membrane of the roof. The presence of water causes a variation in electrical impedance.
 3. Nuclear scan: Utilizing a radioactive isotope device and specialized personnel to determine the presence of water by changes in radiation levels.

Of these methods, only the VFM method provides any early roof leak detection capability. However, VFM tends to have a high rate of false detection when used for early roof leak detection. That is, the impedance levels of the inductive or capacitive reactance between wires can change even if water has not leaked through the roofing membrane. In addition, none of these methods provide a means for detecting intrusion or changes in strain associated with excessive load. Additionally, none provide a means of assurance of insulation and reflective performance of roofs.

With regards to fiber optic sensing, Brillouin, Raman, and interferometer applications are well known and widely deployed; however, none have been suitable for roof applications. This is because existing optical sensing technologies do not provide a means for directing and maintaining moisture at or near the sensing fiber optic strand. Moreover, existing installation practices of sensing fiber optic strands for strain measurements is difficult and labor intensive. Because of installation difficulty, installation costs and lack of assurance of detection of intrusive events (water, temperature, and strain), sensing fibers have not been utilized in roof construction. As a result, there is a continuing need for improved building monitoring systems for detecting roof leaks.

SUMMARY OF THE INVENTION

The present invention may be implemented as a building roof monitoring system that includes a fiber optic sensing filament positioned between a water barrier layer (e.g., roof membrane) and a roof substrate layer of the building roof. The fiber optic sensing filament may be part of a fiber optic sensing mesh layer that includes the filament carried by a water transport layer configured to draw water coming into contact with the water transport layer into contact with the fiber optic filament. An optical analyzer injects laser light into the fiber optic filament and detects changes in propagation of the laser light through the fiber optic filament indicative of water coming in contact with the fiber optic filament to detect a roof leak. A response system including a controller, alarm or remote communication unit operatively connected to the optical analyzer responds to the roof leak detected by the optical analyzer.

The water transport layer may be configured as a number of water transport panels in which the fiber optic filament is sinuously in contact with and carried by the water transport panels. For example, each panel may be in the form of a standard sheet (e.g. 10 foot by 40 foot sheet) or in the form of an elongated length of material unrolled from a roll (10 foot by 100 foot sheet). The fiber optic filament may be woven into the water transport layer or adhered to the water transport layer, for example with tape or an adhesive. The fiber optic filaments carried by the panels are fused from panel to panel to form a continuous fiber optic filament spanning multiple panels to provide desired roof coverage.

The water transport layer typically includes an open weave fabric of stranded fibers having a weave spacing sufficiently large to allow roof adhesive to pass through the water transport layer to adhere the water barrier layer positioned above the water transport layer to the roof substrate layer positioned below the water transport layer. In particular, the weave spacing may be not greater than about one-half of an inch and not less than about one-eighth of an inch.

The fiber optic sensing layer may be assembled by positioning a number of fiber optic sensor panels side by side to form the fiber optic sensor layer. The fiber optic filaments of adjacent panels are then fused together to form a continuous fiber optic filament. The continuity of the continuous fiber optic filament is tested prior to affixing a water barrier layer above the fiber optic sensor layer to position the fiber optic sensor layer between the water barrier layer and the roof substrate layer. The optical analyzer is then calibrated by placing temperature changing devices at known locations above the water barrier layer and calibrating the optical analyzer based on data received by the fiber optic filament caused by the temperature changing devices. For example, the temperature changing devices may be bags of ice in warm weather or a heat gun in cold weather.

In addition, the water transport layer may be in the form of water transport tape and the fiber optic filament may be adhered to the water transport tape in the regions of joints between portions of the roof substrate.

It should also be understood that many other advantages and alternatives for practicing the invention will become apparent from the following detailed description of the preferred embodiments and the appended drawings.

DETAILED DESCRIPTION

Figure 1:
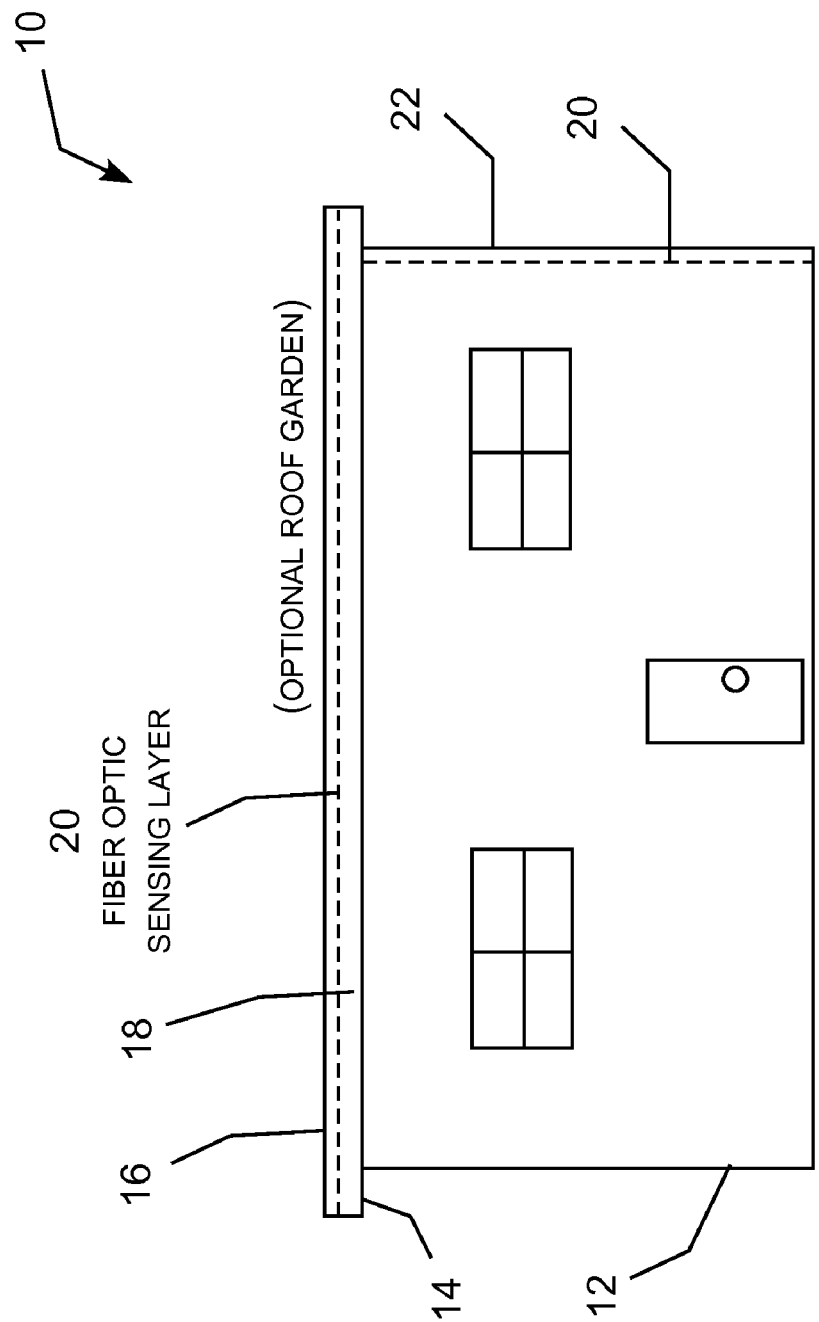
FIG. 1 is a conceptual illustration of a building having a fiber optic building monitoring system.

The present invention provides a fiber optic building monitoring system that uses a fiber optic sensing layer positioned between the water barrier layer and the roof substrate layer to detect roof leaks. This system provides a multitude of advantages in roof monitoring systems by solving the challenges of utilizing fiber optic sensing for water detection, direct temperature measurement, and strain measurement. The fiber optic building monitor is well adapted to roof leak monitoring because it does not interfere with the roof system performance, is simple to install, and has a variety of options for use with optical sensing technologies (e.g., Brillouin, Raman, optical frequency domain reflectometry, etc.)

Exploiting the known phenomenon associated with fiber optics, the fiber optic filament carried by the sensing mesh conveys the linear distance information of temperature and strain. By correlating the linear distance to the actual installation layout, localized changes in temperature indicated by the optical sensor are mapped onto an image of the roof to give a clear indication of the physical location of a leak. Changes in temperature can also be indicative of loss in performance of solar reflective index (SRI) of a LEEDS® roof. Strain changes are commonly associated with security and water intrusion detection, but excessive weight build up (as in a severe snowstorm) can also cause dramatic changes in strain that can result in ultimate structural failure. The fiber optic building monitoring system can detect any of these conditions.

For the building roof leak detection application, roof leak detection relies on localized cooling or heating induced in the fiber optic filament caused by water coming in contact with the fiber optic filament. The fiber optic sensing layer may therefore include a water transport mesh that draws water into contact with the optical fiber and provides extended contact of the moisture with the sensing fiber to aid in detection or roof leaks. To exhibit the desired water transport properties, the water transport layer is made from an open weave fabric of stranded fibers that allows the mesh to transport water toward the fiber optic strand. The type of mesh material and the overall weave of the water transport mesh may vary based on the type of roof system to provide the desired water transportation characteristics (e.g., wicking, non-wicking channeling) for the particular roof.

A roof membrane system may be generally defined as any system including at least a single ply of material designed to impede the flow of water. In today's market, there has been a great deal of emphasis in using single ply roof membranes utilizing many differing chemical compounds formed into wide sheets. Compounds such as EPDM (Ethylene-Propylene-Diene-Monomer Roofing), PVC (Polyvinyl Chloride), TPO (Thermoplastic Olefin), and CPVC (Chlorinated Polyvinyl Chloride) and their respective generational upgrades are utilized. At present, the most popular in the single ply membrane systems are the EPDM and TPO sheets. Popularity has been due to total installed cost, performance, much less intensive installation labor, and good marketing techniques.

Installation of the prominent EPDM and TPO systems, as with the other non-asphalt based single ply systems, are generally in one of three methods. A first installation technique is loose laid roof membrane with ballast. No fastening is required other than roof ballast weight per square foot to meet code wind load uplift requirements. A second installation technique is mechanically fastened, in which continuous metal strips fasten the roof membrane to substrate at specific intervals. A third installation technique is fully adhered systems, in which complete adhesive coverage attaches the membrane to underlying roof substrate. The fiber optic building monitoring system works with any of these roof systems.

In addition, in an ever evolving ecologically concerned construction marketplace, some old philosophies have returned, such as planting a garden on the roof. Installing a membrane over insulation, then covering the membrane with engineered soil to various depths required for the planting (low shrubs, flowers, to rather large trees) and pedestrian walkways has become more commonplace. This gives the property owner additional "Green space" which aides in the ecology and the granting of LEED® (Leadership in Energy & Environmental Design) points for these concerned owners. Finding a leak in this roof type is a real nightmare. The fiber optic building monitoring system is well adapted to detect leaks occurring in this type of garden roof system.

Three techniques have been adopted for implementation of the fiber optic roof system. A first approach includes a full layer mat system including a non-woven fabric, which may be used with loose laid/ballasted and mechanically attached roof membranes. A fabric utilizing needle-punched polyester fabric (generally 10 foot widths) in full coverage may be applied over the entire roof with interwoven or adhesive attachment of the optic strand. The spacing of the optic strand is based on sensitivity requirements. It is believed that a resolution to the typical substrate panel of 4'×8' is sufficient for most roofs. In these cases, the fibers will match the width or length of the substrate panel (e.g. every 48" or 96") depending on the layout of the substrate panels. One square meter (1 $m^2$) resolution to the leak event is regarded as more accurate, but requires closer optical fiber spacing. For 1 $m^2$ resolution on a 10' wide panel, three parallel rows of sensing fiber will be installed no more than 39" from each other. This system is installed by unrolling the non-woven mat with spaced optical fiber over entire roof surface substrate just prior to roof membrane installation, securing the mat as required for temporary placement until roof membrane installation, provide for roof penetrations as needed, splicing in any additional lengths of optical fibers to allow for large penetrations, splicing optical fiber ends together to form a complete loop, testing for continuity, and running optical fiber ends to the termination point (optical switch or analyzer). This system has the highest cost factor of the three techniques evaluated.

A second system includes a full layer mat system using a woven fabric with loose laid/ballasted, mechanically attached, and fully adhered roof membranes. This system uses fabric utilizing one or more strand materials in a woven fabric (base fabric weft/warp not more than ½" by ½", not less than ⅛" by ⅛", and generally 10 foot widths) in full coverage over the entire roof with interwoven, adhesive, or tape attachment of the optic strand. The optic strand spacing is based on sensitivity requirements. As with the non-woven full layer mat approach, one square meter (1 $m^2$) resolution to the leak event is regarded as extremely accurate, but requires closer spacing of the optical fiber. For 1 $m^2$ resolution parallel rows of sensing fiber will be installed no more than 39" from each other. It is generally accepted that a less accurate resolution to the typical substrate panel of 4'×8' is sufficient for most roofs.

In these cases, the fibers will match the width or length of the substrate panel (e.g. every 48" or 96") depending on the layout of the substrate panels. This system is installed by unrolling the woven mat with spaced optical fiber over the entire roof surface substrate just prior to roof membrane installation, securing the mat as required for temporary placement until roof membrane installation, providing for roof penetrations as needed, splicing in any additional lengths of optical fibers to allow for large penetrations, splicing optical fiber ends together to form a complete loop, testing for continuity, and running optical fiber ends to the termination point (optical switch or analyzer). This system has an intermediate cost factor of the three techniques evaluated.

A third system includes a tape system used with loose laid/ballasted, mechanically attached, and fully adhered roof membranes. This system woven uses fabric tape in 4 inch to 6 inch wide rolls containing a strand mesh material in a woven fabric (stranded mesh weft/warp typically not more than ½" by ½", not less than ⅛" by ⅛") with a single optical filament running in the center of the tape. The optical fiber may be interwoven or adhesive attached to the tape. The woven fabric tape has slight adhesive for "tacking" to the roof substrate and is typically laid along the top substrate layer of the roof insulation board, redirected as needed to cover all roof penetrations or protection layer at the joints. This system is installed by adhering the tape carrying the fiber optic filament along the top substrate layer of the roof insulation board or protection layer at the joints over entire the roof substrate just prior to roof membrane installation, splicing optical fiber ends together to form a complete loop, testing for continuity, and running optical fiber ends to the termination point (optical switch or analyzer). This system has the lowest cost factor of the three techniques evaluated.

Many different kinds, types, and blends of strands used in making an open weave fabric or needle punched fabric are available. Strand materials are based on using natural occurring fiber, (e.g., hemp and cotton), synthetic fibers such as fiberglass, polyethylene, polypropylene, nylon, polyester, rayon, HDPE, (High Density Polyethylene Polymer), and others. Certain combinations using two or more of certain fibers can be used in certain applications. HPDE has shown that it does not work well in this system application due to several reasons including extreme difficulty in material thicknesses available, securing material flat due to the inherent fabric memory, and lack of channeling ability. Rayon does not possess the ability for channeling desired.

Natural fibers work quite well in roof membrane systems not fully adhered. Those include loose laid/ballasted roof membranes and mechanically attached roof membrane systems. Synthetic materials including fiberglass, polyethylene, polypropylene, and nylon also possess the desired characteristics. Blends may be used and additional strands may be included to provide the desired performance in all three roof membrane installation methods.

In a loose laid ballast and mechanically attached roof application, the fiber optic sensing layer does not significantly affect the attachment of the water barrier layer to the roof substrate layer. As a result, there is fairly wide latitude in the selection of the water transport material for these types of roofs. 100% polyester fibers for the thread of the sensing mesh provides excellent channeling of water, with little to no absorption. Further its melt temperature of 509° F. is well suited for summer roof temperatures (roof temperatures at insulation layer under roof membrane reach temperatures less than 175° F.). The thread width can be very low with a narrow ⅛" by ⅛" weave spacing. A weight of 3.3 osy (ounces per square yard) is sufficient for the water transport layer.

In an adhered roof application, the water transport mesh is more critical and selected to have a sufficient weave spacing to allow typical roof adhesives to pass through the mesh to bind the water barrier layer to the roof substrate. At the same time, the mesh fibers and the fiber optic filament should not become completely embedded in the roof adhesive, which would inhibit water from coming in contact with the water transport layer. A blend of 50% polyester and 50% cotton fibers forming threads provides enough cotton to channel the water the length of the sensing mesh to the optical sensing fiber. Having weave spacing in the range of about ½" to ⅛" has been found to be suitable for use with typical fully adhered roof systems with little interference with the adhesion of the roof membrane to the substrate. A wider spacing allows small penetrations in the roof membrane to go undetected and a smaller spacing can impede the flow of adhesive through the mesh. A heavier weight of 6 osy is a suitable volume of cotton and polyester thread for adhered roof systems. This type of mesh is also compatible with loose laid ballast and mechanically attached roof systems. Therefore, a fiber optic sensing layer with this type of water transport mesh is versatile enough to provide a universal product for use with loose laid, mechanically attached, and adhered roof systems. For example, this type of mesh allows asphalt (petroleum based), coal tar, metal, single ply systems, sprayed-foam, mechanically adhered, and rolled-on roof systems to be installed over the fiber optic sensing layer without reducing the performance of the roof.

The fiber optic sensing strand may be an open ended or looped design. While bare single mode fiber ($9/125$ µm) will work, it provides no protection against cleaving. A preferred fiber will have a protective cladding attached to the fiber optic strand such as the Aramid reinforced 900 µm tight buffer fiber with bend insensitive single mode fiber from AFL Telecommunications: commercially known as the 900 Micron Mini-Link II. At least one end of the optical fiber is attached to an optical analyzer, either directly or through an optional switch. The optical sensing fiber used in this product may be bare fiber, clad fibers, fiber in tubing, or any combination thereof in order to best meet the needs and challenges of each application. The 900 Micron Mini-Link II works very well with Brillouin based optical sensors. However, the invention is not limited the use of a specific fiber optic strand type or package. By utilizing the sensing mesh technology with optical sensor, measurements that are taken at time of installation or any subsequent measurement(s) can be monitored, compared or referenced to detect changes over the life of the object being measured.

Temperature changes in the areas of the sensing mesh with sensing fiber will cause localized changes in the sensing fiber. This is detected by known optical sensing technology (e.g., Brillouin, Raman, OFDR etc). Linear optical fiber distance from the light source/detector is then related to the known installation layout of the optical fiber to identify the location of the source of the strain on the optical fiber. This provides time stamped referencing which in turn allows early intervention to correct causes of leakage, changes in insulation values, changes in strain values, or load changes.

The optical analyzer uses light pulses to interrogate the condition of the sensing fibers. Utilizing optical back reflections, it is possible to determine the temperature of the sensing fiber along the entire length of the sensing fiber. Several sensing technologies are available. The Brillouin back reflections can be spontaneous from open-ended and are known as Brillouin Optical Time Domain Reflectometry (B OTDR) systems. Stimulated Brillouin systems may use either an open-ended system or a looped system. Stimulated Brillouin approach is known as a Brillouin Optical Time Domain Analyzer (B-OTDA) because the impact of the Brillouin back reflection is measured instead of the actual Brillouin back reflection itself. Raman OTDR (R-OTDR) may also be used to measure temperature changes by measuring the Raman back reflection. Rayleigh back reflections may be used to measure temperature via a method known as Optical Frequency Domain Reflectometry (OFDR). The sensing fiber used with the sensing mesh in section is selected to best match the method of optical sensing be used by the optical analyzer.

The measurements from the optical analyzer are taken against known temperature conditions and physical location of the fiber. This data is correlated via software to form complete image of the roof being monitored and physical layout of the sensing mesh with fiber optic sensor. Optionally, the optical analyzer can also provide alarm data and reports to an external controller, operations center etc. The optical analyzer measurements are provided to the controller for monitoring, alarming, local and remote logging, local and remote diagnostics. The controller establishes all test, measurement sequences, monitoring, dates, times, duration, etc. It also controls the flow of data between the optical analyzer and external alarm monitoring and reporting software.

Turning now to the drawings, FIG. 1 is an illustrative view of a fiber optic building monitoring system 10 installed on a building 12, which provides a representative environment in which the fiber optic building monitoring system may be employed. In this particular illustration, the building 12 includes an above ground structure carrying a protective roof 14. The roof includes a water barrier layer 16, such as a roof membrane, attached to a roof substrate 18, such as insulation tiles or decking. A fiber optic sensing layer 20 is positioned between the water barrier layer 16 and the roof substrate layer 18. The fiber optic sensing layer 20 may also be installed under the outer layer 22 of an upright wall or in any other location where monitoring of water infiltration or other sources of strain in the fiber optic filament is desired. Although the fiber optic building monitoring system may be used to detect a wide range of conditions inducing strain in the fiber optic filament, the following example describes roof leak detection as an illustrative example of the technology.

Figure 2:
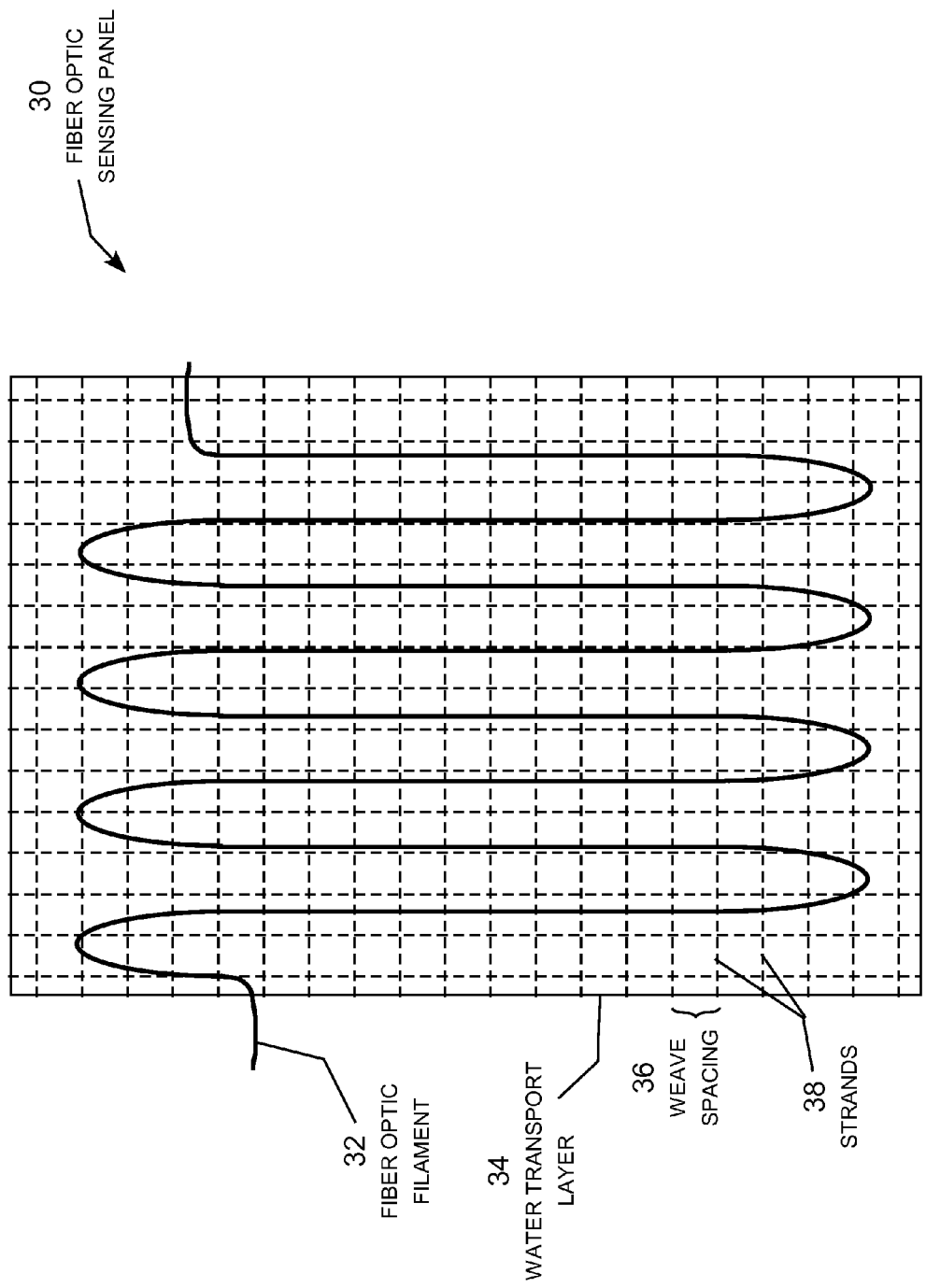
FIG. 2 is a conceptual illustration of a fiber optic sensing panel including a sinuous fiber optic filament carried by a water transport mesh.
Figure 3:
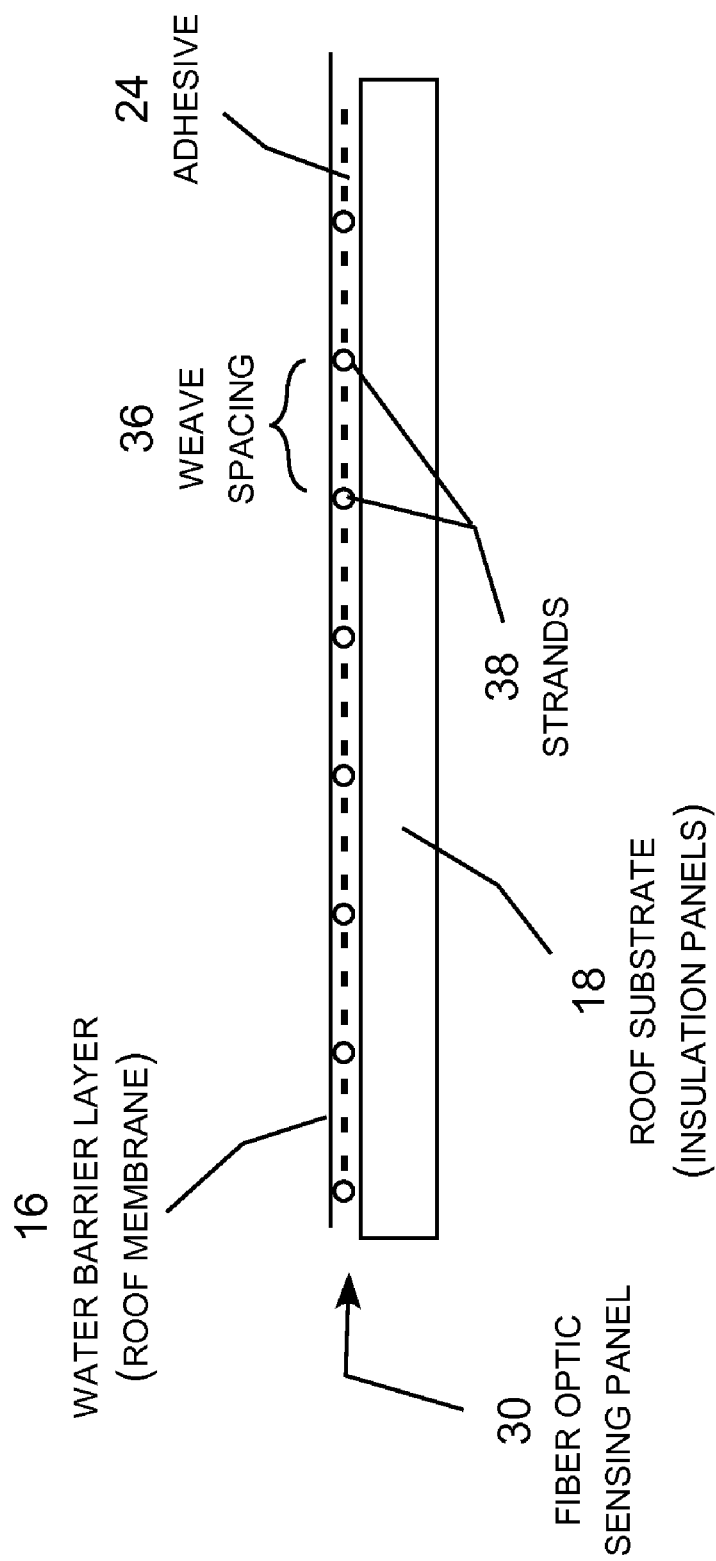
FIG. 3 is a conceptual side view of the fiber optic sensing panel incorporated into a building roof.

FIG. 2 is a conceptual illustration of a fiber optic sensing panel 30 including a sinuous fiber optic filament 32 carried by a water transport mesh 34. The fiber optic sensing layer may be provided in rolls and the panel 30 may be an unrolled length of the material. FIG. 3 is a conceptual side view illustrating the fiber optic sensing panel 30 from the side. The mesh has a weave spacing 36 between the strands 38 sufficient to allow typical roof adhesives to pass through without substantially reducing the adhesion of the material above the mesh (e.g., roof membrane) to the layer below the mesh (e.g., underlying insulation panels or roof decking). The ability to pass roof adhesive in an important property of the fiber optic sensing layer 20 for fully adhered roof applications that allows it to be installed directly between the water barrier layer 16 and the roof substrate 18 on roofs utilizing roof adhesive. To allow this type of installation without reducing the performance of the roof, the fiber optic sensing mesh 20 is sufficiently porous to allow typical roof adhesive 24 to flow through the mesh to the underlying roof substrate therefore allowing the adhesive to be installed over the fiber optic sensing mesh without significantly reducing the adhesion of the water barrier layer 16 to the roof substrate 18. Although the weave spacing 36 may vary for different adhesives, weave spacing in the range of about ½" to ⅛" has been found to be suitable for use with commonly used roof adhesives. This makes the fiber optic sensing mesh 20 compatible with asphalt (petroleum based), coal tar, metal, single ply systems, sprayed-foam, mechanically adhered, and rolled-on roof systems.

Figure 4:
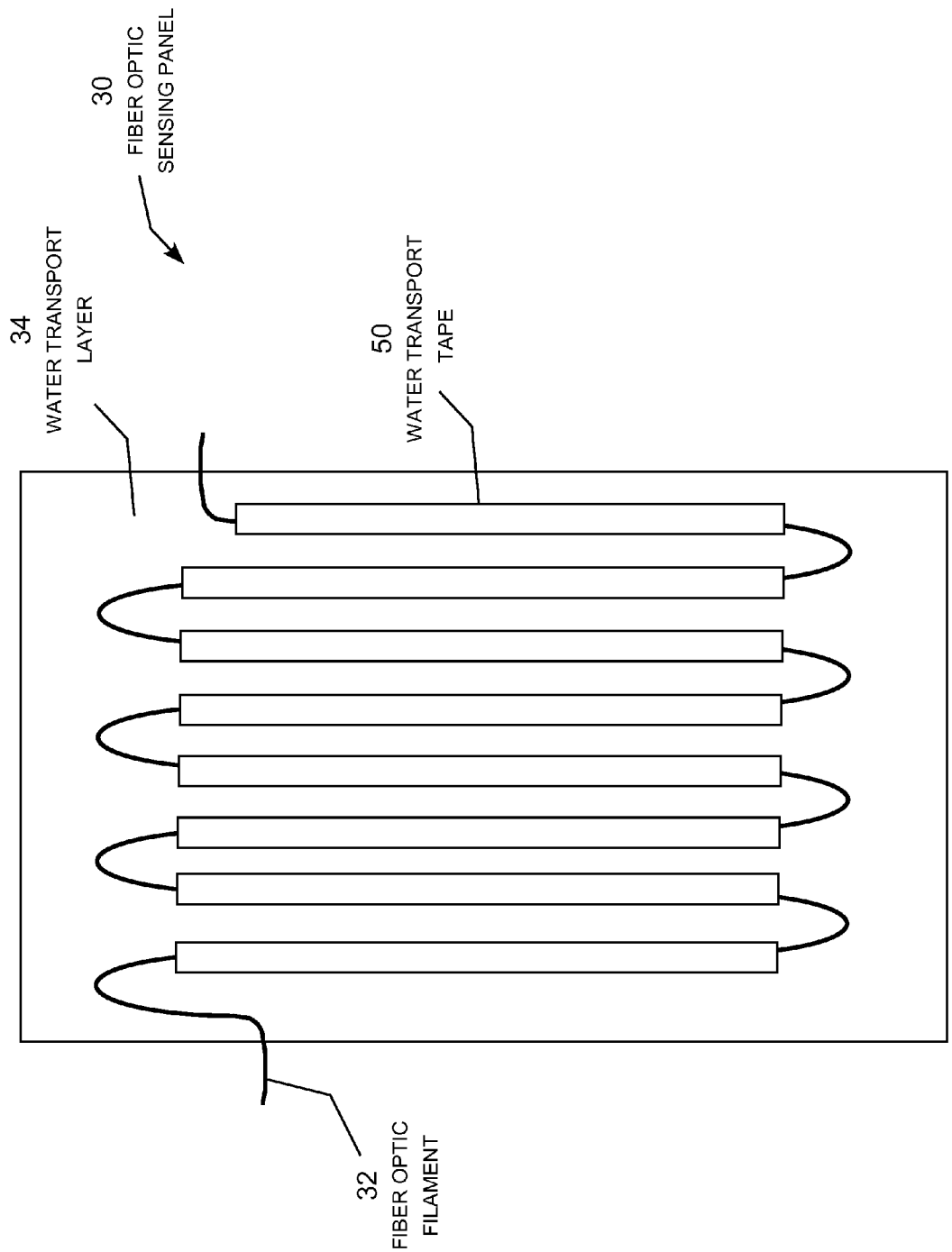
FIG. 4 is a conceptual illustration of a fiber optic sensing panel including a sinuous fiber optic filament attached to a water transport mesh with water transport tape.

The sinuous fiber optic filament 32 may be woven into the strands 38 or it may be secured to the water transport mesh 34 with an adhesive or water transport tape 50 as shown in FIG. 4. Typical mesh type drywall tape formed of a mesh weave with about ¼" mesh spacing has been found to be suitable for this application.

Figure 5:
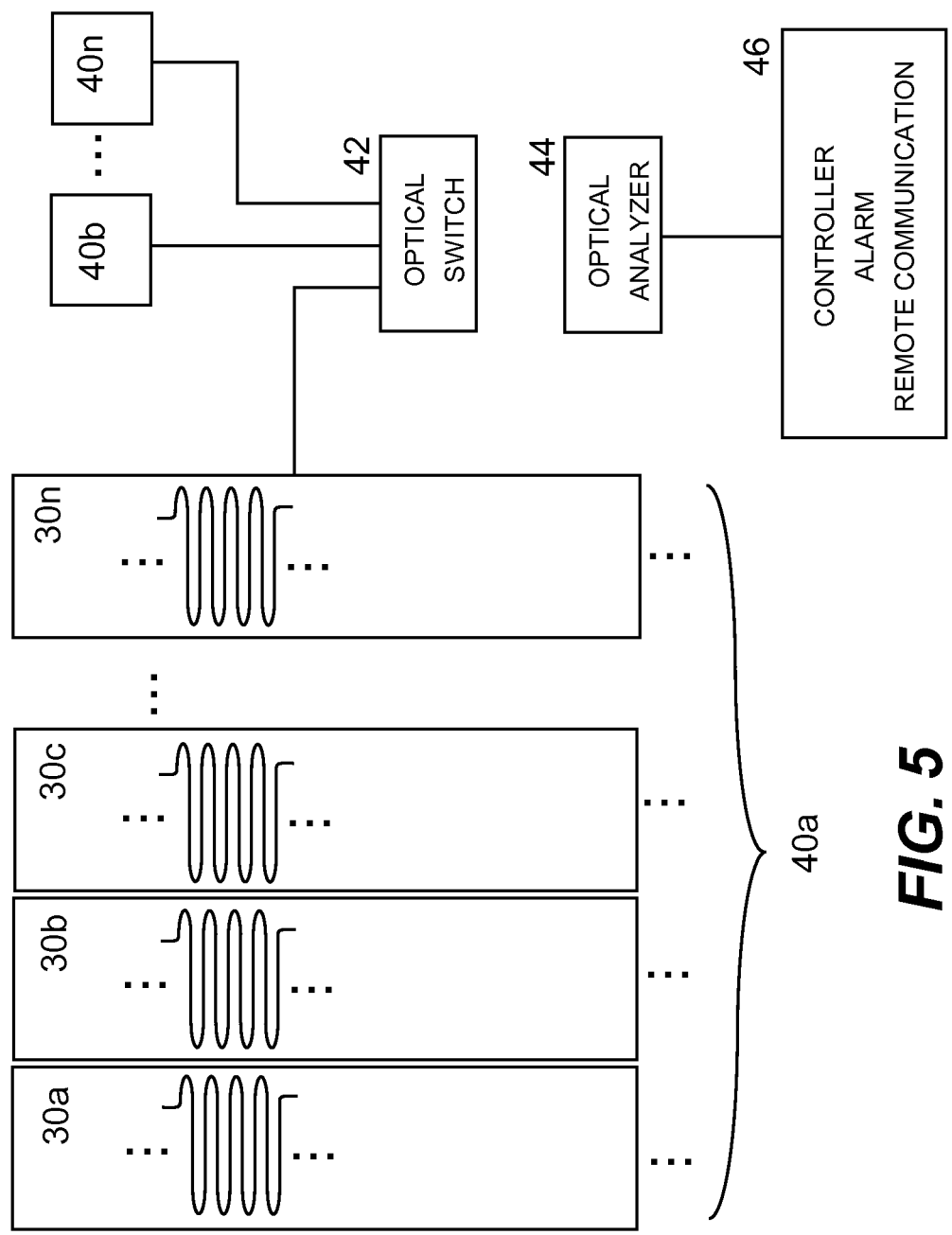
FIG. 5 is a conceptual illustration a fiber optic building monitoring system including multiple fiber optic sensing panels.

FIG. 5 is a conceptual illustration a fiber optic building monitoring system including multiple fiber optic sensing panels 30a-n, which may be elongated panels unrolled from rolls of the material. The regular panel pattern shown is FIG. 5 is merely illustrative. That is, the fiber optic sensing layer is customized to match the shape of the roof being monitored of any desirable shape and configuration of segments or panels linked together to form a mesh carrying a continuous fiber optic filament. In this manner, any desired area can be monitored with the fiber optic monitoring system.

The optical filaments from each sub section 30a-n are fusion spliced together to form a continuous optical filament. The continuous fiber optical filament is operatively connected to an optical analyzer 44, which is in turn connected to a response system 46 that typically includes one or more of a controller, an alarm, and remote communications equipment. The optical analyzer 44 injects laser light into the optical filament and detects changes in the propagation characteristics of the light propagating in the fiber indicative strain imposed on the fiber. The strain is typically caused by changes in temperature, which typically results from water coming in contact with the filament indicating a roof leak. Other types of strain causing conditions may also be detected, such as a heavy snow load on the roof, loss of insulation properties of the roof, heavy objects located on the roof, and so forth. For looped measurement system, both ends of the fibers are returned to the optical analyzer. For open-ended measurement systems, only one end of the fiber is required to be returned to the optical analyzer.

As an option, the panels 30a-n may form a first zone 40a of the roof monitoring system and an optical switch 42 may be used to allow multiple fibers from multiple zones 40a-n to be selected for measurement. If used, the optical switch 42 is placed between the fiber optic sensing zones 40a-n and the optical analyzer 40. The optical switch selects among a number of sensing fibers of the zones 40a-n, which may be alternately connected to the optical analyzer at any given measurement. The optical switch may be controlled externally from the optical analyzer or via some other remote command method such as the controller.

Figure 6:
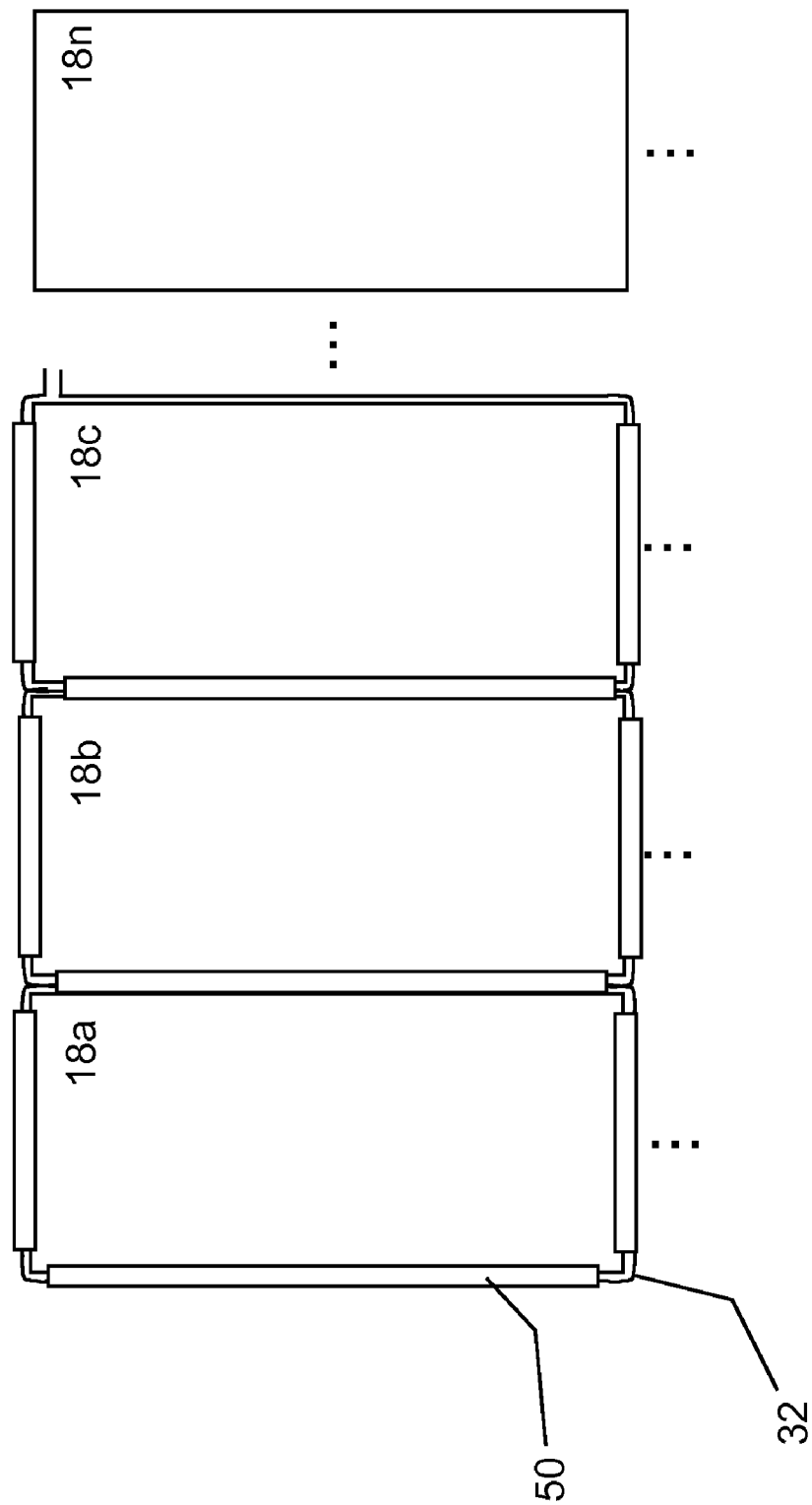
FIG. 6 is a conceptual illustration an alternate fiber optic building monitoring system.

FIG. 6 is a conceptual illustration an alternate arrangement for a fiber optic building monitoring system. In this alternative, the optical fiber 32 is positioned at the joints between adjacent panels 18a-n of the underlying roof substrate using water transport tape 50. All of the joints in the roof substrate may be covered to provide comprehensive monitoring of the joints in the roof substrate. In addition, the fiber optic filament could be taped to roof decking or any other type of roof substrate, typically using water transport tape, in any other desired configuration.

Figure 7:
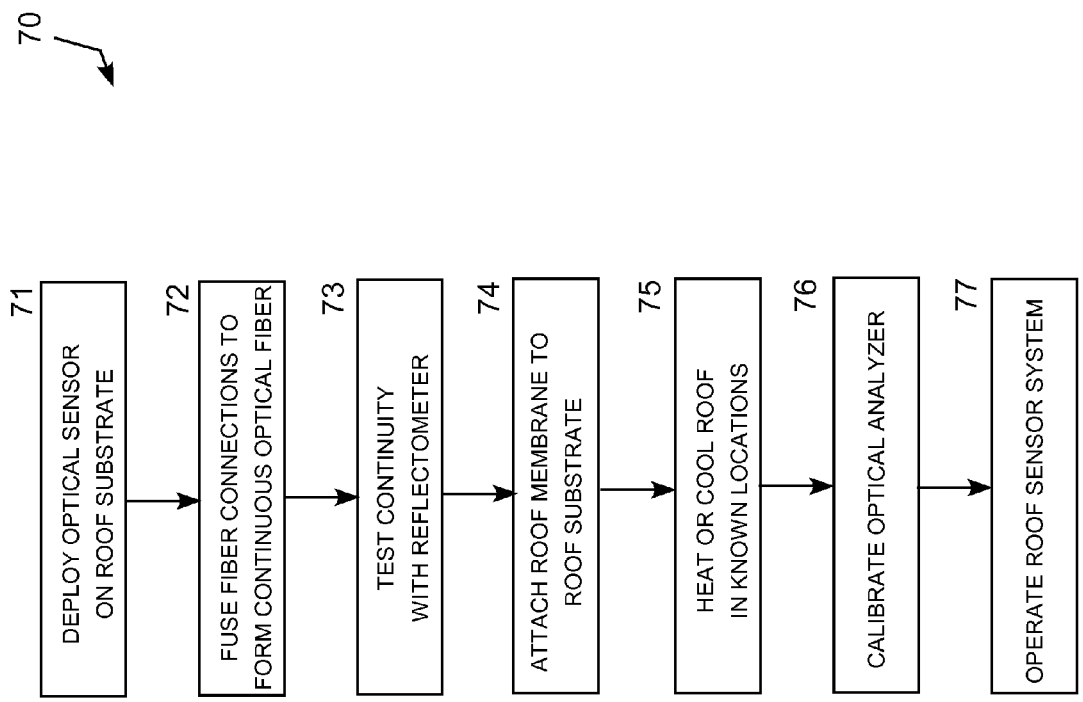
FIG. 7 is a logic flow diagram illustrating a method for testing and calibrating a fiber optic sensor system.

FIG. 7 is a logic flow diagram illustrating a method for testing and calibrating a fiber optic sensor system. In step 71, the optical sensor is deployed on the roof substrate. This is typically accomplished by rolling out a layer of the optical fiber mesh or taping the optical fiber in the regions of the joints between adjacent portions of the roof substrate. Step 71 is followed by step 72, in which the sections of the optical fiber are fusion spliced to form a continuous fiber. Step 72 is followed by step 73, in which the continuity of the fiber is tested using a reflectometer prior to installation of the water barrier layer over the roof substrate layer. Step 73 is followed by step 74, in which the water barrier layer is installed over the roof substrate layer and the fiber optic sensor layer. Step 74 is followed by step 75, in which the roof is heated or cooled in known locations. For example, in the summer ice bags can be placed on the roof to cool the roof in known locations. Similarly, in the winter a heat gun can be used to heat the roof in know location. Step 75 is followed by step 76, in which the optical analyzer is calibrated using by detecting the strain induced in the optical fiber by heating or cooling the roof in the known locations and using this information to correlate the optical fiber measurements onto the physical layout of the roof. Step 76 is followed by step 77, in which the roof sensor system to ready for operation.

In view of the foregoing, it will be appreciated that present invention provides significant improvements in building roof monitoring systems. It should be understood that the foregoing relates only to the exemplary embodiments of the present invention, and that numerous changes may be made therein without departing from the spirit and scope of the invention as defined by the following claims.

The invention claimed is:

1. A building roof monitoring system comprising:
   a fiber optic filament positioned between a water barrier layer and a roof substrate layer of a building roof;
   a water transport layer in contact with the fiber optic filament having a weave spacing sufficiently large to allow roof adhesive to pass through the water transport layer to adhere the water barrier layer positioned above the water transport layer to the roof substrate layer positioned below the water transport layer;
   an optical analyzer for injecting laser light into the fiber optic filament and detecting a change in propagation of the laser light through the fiber optic filament indicative of water coming in contact with the fiber optic filament to detect a roof leak;
   a response system comprising a controller, alarm or remote communication unit operatively connected to the optical analyzer configured to respond to the roof leak detected by the optical analyzer.

2. The building roof monitoring system of claim 1, wherein the water transport layer comprises an open weave fabric comprising stranded fibers in contact with the fiber optic filament configured to draw water coming into contact with the water transport layer into contact with the fiber optic filament.

3. The building roof monitoring system of claim 2, wherein the water transport layer has a weave spacing sufficiently large to allow roof adhesive to pass through the water transport layer to adhere the water barrier layer positioned above the water transport layer to the roof substrate layer positioned below the water transport layer.

4. The building roof monitoring system of claim 2, wherein the water transport layer comprises a plurality of water transport panels and the fiber optic filaments are fused from panel to panel to form a continuous fiber optic filament spanning multiple panels to provide desired roof coverage.

5. The building roof monitoring system of claim 1, wherein the weave spacing is not greater than about one-half of an inch and not less than about one-eight of an inch.

6. The building roof monitoring system of claim 1, wherein the water transport layer comprises a water transport panel and the fiber optic filament is sinuously in contact with and carried by the water transport panel.

7. The building roof monitoring system of claim 1, wherein the fiber optic filament is woven into the water transport layer.

8. The building roof monitoring system of claim 1, wherein the fiber optic filament is taped onto the water transport layer.

9. The building roof monitoring system of claim 1, wherein the fiber optic filament is adhered to water transport layer.

10. A method for monitoring a building roof, comprising the steps of:
    positioning above a roof substrate layer a fiber optic sensor layer comprising:
       a fiber optic filament; and
       a water transport layer in contact with the fiber optic filament configured to draw water coming into contact with the water transport layer into contact with the fiber optic filament, the water transport layer having a weave spacing sufficiently large to allow roof adhesive to pass through the water transport layer to adhere the water barrier layer positioned above the water transport layer to the roof substrate layer positioned below the water transport layer;
    affixing a water barrier layer above the fiber optic sensor layer to position the fiber optic sensor layer between the water barrier layer and the roof substrate layer;
    operatively connecting an optical analyzer to the fiber optic filament that injects laser light into the fiber optic filament and detects a change in propagation of the laser light through the fiber optic filament indicative of water coming in contact with the fiber optic filament to detect a roof leak, and
    operatively connecting a response system to the optical analyzer comprising a controller, alarm or remote communication unit configured to respond to the roof leak detected by the optical analyzer.

11. The method of claim 10, further comprising the step of providing the water transport layer with the fiber optic filament woven into the water transport layer.

12. The method of claim 10, further comprising the step of providing the water transport layer with the fiber optic filament taped to the water transport layer.

13. The method of claim 10, further comprising the steps of:
    adhering the water barrier layer to the roof substrate layer with roof adhesive by applying the roof adhesive above the water transport layer and positioning the water barrier above the roof adhesive to allow the roof adhesive to bond to the water barrier layer, pass through the water transport layer, and bond to the roof substrate layer.

14. The method of claim 13, wherein the weave spacing is not greater than about one-half of an inch and not less than about one-eight of an inch.

15. The method of claim 10, further comprising the step of connecting a controller, alarm or remote communication to the optical analyzer configured to respond to the roof leak detected by the optical analyzer.

16. The method of claim 10, further comprising the step of:
    positioning a plurality of fiber optic sensor panels side by side to form the fiber optic sensor layer;
    fusing the fiber optic filaments of adjacent panels together to form a continuous fiber optic filament; and
    testing continuity of the continuous fiber optic filament.

17. The method of claim 16, further comprising the step of:
    placing temperature changing devices at know locations above the water barrier layer; and calibrating the optical analyzer based on data received by the fiber optic filament caused by the temperature changing devices.

18. A building roof monitoring system comprising:
a fiber optic sensing layer positioned between a water barrier layer and a roof substrate layer of a building roof;
the fiber optic sensing layer comprising a fiber optic filament carried by water transport tape adhered in the region of a joint between adjacent portions of the roof substrate layer;
an optical analyzer for injecting laser light into the fiber optic filament and detecting a change in propagation of the laser light through the fiber optic filament indicative of water coming in contact with the fiber optic filament to detect a roof leak;
a response system comprising a controller, alarm or remote communication unit operatively connected to the optical analyzer configured to respond to the roof leak detected by the optical analyzer.

19. The building roof monitoring system of claim 18, wherein the water transport tape comprises an open weave fabric comprising stranded fibers.

20. The roof monitoring system of claim 18, wherein the roof substrate layer comprises a plurality of roof panels and the water transport tape carrying the fiber optic filament is adhered in the regions of a plurality joints between adjacent roof panels.

* * * * *